United States Patent
Fellin et al.

(10) Patent No.: US 10,684,460 B2
(45) Date of Patent: Jun. 16, 2020

(54) OPTICAL ADAPTER CONNECTABLE TO AN IMAGE ACQUISITION DEVICE, IN PARTICULAR INTENDED TO BE USED FOR MICROSCOPIC OBSERVATION

(71) Applicant: FONDAZIONE ISTITUTO ITALIANO DI TECNOLOGIA, Genoa (IT)

(72) Inventors: Tommaso Fellin, Manesseno (IT); Andrea Antonini, Alfonsine (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 4 days.

(21) Appl. No.: 15/770,099

(22) PCT Filed: Oct. 19, 2016

(86) PCT No.: PCT/IB2016/056265
§ 371 (c)(1),
(2) Date: Apr. 20, 2018

(87) PCT Pub. No.: WO2017/068501
PCT Pub. Date: Apr. 27, 2017

(65) Prior Publication Data
US 2018/0307029 A1    Oct. 25, 2018

(30) Foreign Application Priority Data
Oct. 21, 2015   (IT) .................. 102015000063675

(51) Int. Cl.
*G02B 27/02*     (2006.01)
*G02B 21/36*     (2006.01)
(Continued)

(52) U.S. Cl.
CPC ........ *G02B 21/361* (2013.01); *A61B 1/00126* (2013.01); *G02B 21/0008* (2013.01);
(Continued)

(58) Field of Classification Search
CPC .. G02B 21/361; G02B 21/02; G02B 21/0008; G02B 25/002; A61B 1/00126; H04M 1/0264; G03B 17/565
See application file for complete search history.

(56) References Cited

U.S. PATENT DOCUMENTS

| 7,586,675 B2 | 8/2009 | Sander |
| 2005/0030647 A1 | 2/2005 | Amanai |

(Continued)

FOREIGN PATENT DOCUMENTS

| DE | 102005036486 A1 | 1/2007 |
| WO | 2012/058641 A2 | 5/2012 |

(Continued)

OTHER PUBLICATIONS

Int'l Search Report and Written Opinion from Int'l Appl'n No. PCT/IB2016/056265, dated Apr. 5, 2017.
(Continued)

*Primary Examiner* — Alicia M Harrington
(74) *Attorney, Agent, or Firm* — Merchant & Gould P.C.

(57) ABSTRACT

An optical adapter includes a support, which can be removably coupled to an image acquisition device. The support has a substrate made of substantially transparent material. The substrate has a proximal surface intended for facing towards the device and a distal surface located at a distance from the proximal surface and intended for facing towards an object to be observed. The support also has a lens located in a seat obtained in the substrate and facing towards the objective of the device. In addition, the support has a reflector located laterally relative to the lens and arranged for facing towards
(Continued)

a light source integrated into the device and conveying the light emitted by the light source in a transversal direction towards the lens and past the distal surface.

11 Claims, 7 Drawing Sheets

(51) Int. Cl.
*G02B 21/00* (2006.01)
*H04M 1/02* (2006.01)
*A61B 1/00* (2006.01)
*G02B 25/00* (2006.01)
*G02B 21/02* (2006.01)
*G03B 17/56* (2006.01)

(52) U.S. Cl.
CPC ........... *G02B 21/02* (2013.01); *G02B 25/002* (2013.01); *H04M 1/0264* (2013.01); *G03B 17/565* (2013.01)

(56) References Cited

U.S. PATENT DOCUMENTS

2014/0362239 A1   12/2014   Larson
2016/0296111 A1*  10/2016   Russo ..................... A61B 3/12

FOREIGN PATENT DOCUMENTS

WO   WO2015071779   *  5/2015   ............ G03B 17/56
WO   2015/087232 A1    6/2015

OTHER PUBLICATIONS

Smith et al., "Cell-Phone-Based Platform for Biomedical Device Development and Education Applications," PLoS ONE, vol. 6, issue 3, 11 pages (Mar. 2011). Available at: https://doi.org/10.1371/journal.pone.0017150.

* cited by examiner

OPTICAL ADAPTER CONNECTABLE TO AN IMAGE ACQUISITION DEVICE, IN PARTICULAR INTENDED TO BE USED FOR MICROSCOPIC OBSERVATION

This application is a National Stage Application of International Application No. PCT/IB2016/056265, filed 19 Oct. 2016, which claims benefit of Serial No. 102015000063675, filed 21 Oct. 2015 in Italy and which applications are incorporated herein by reference. To the extent appropriate, a claim of priority is made to each of the above disclosed applications.

TECHNICAL FIELD

The present invention relates to an optical adapter which can be coupled to an image acquisition device, in particular for microscopic observation.

BACKGROUND ART

Optical adapters are known in the industry which can be coupled to an image acquisition device, in particular for microscopic observation.

This adapter typology allows transforming an image acquisition device, e.g. a generic cellular telephone (typically a so-called smartphone) or a tablet, into a high-resolution microscope. In particular, electronic devices such as smartphones and tablets have an integrated photographic optical system, which is often capable of changing its focal distance (mems|cam™ Technologies autofocus system or voice coil motor). Of course, the optics of such devices is designed for macroscopic photographic applications. In order to switch to high-resolution microscopic observation, it is necessary to use a lens with high numerical aperture as a terminal element of the optical system, before the sample to be analyzed.

Generally, microscopy optics is characterized in that it can increase the image resolution in order to discern microscopic details. The technical feature that determines the resolution of a microscope, in the absence of any aberrations, is the numerical aperture of the objective lens.

As far as the lens is concerned, as is known, its numerical aperture (NA) is given by the following formulae: $NA = n \sin(\alpha)$ and $\alpha = \arctan(D/2f)$, where f is the focal length of the lens and D is the aperture of the objective lens. Therefore, in order to obtain a high resolution, the ratio between diameter and focal length needs to be high. For minimal apertures like those of the cameras typically integrated into smartphones and tablets, the diameter is very small, and hence the focal length of the lens needs to be very short.

Resolution also depends on the aberrations introduced by the optics. The smaller the dimensions, the more any construction defects are influential and the more the aberrations introduced by the lenses become significant. For this reason, the choice of the lens type and construction is particularly important.

The purpose of the above-mentioned adapter is to make the microscopic world (i.e. with a resolution in the order of a micron) available to anyone into a generally compact design. Such an adapter can be used for various applications, from hobbies to analyses in different professional fields, where "in-field" use (i.e. outside a laboratory) of a microscope may be necessary as a working tool. In addition, such adapters can also find application for medical investigations in developing countries, since they generally imply low production costs.

Adapters generally comprise macroscopic lenses and other macroscopic elements integrated with the optics of the image acquisition device, which typically is a cell phone. However, adapters of this kind are not readily usable and, most importantly, are significantly bulky. By way of example, the following will list a number of disclosures concerning known adapters, which however suffer from several drawbacks.

Patent publication US 2014/0362239 A1 discloses a lens structure that includes an elastomer formed as a lens. The lens has a planar surface and a curved surface opposed to the planar surface. The elastomer of the lens structure may be formed of a base polymer polydimethylsiloxane (PDMS) material. When the lens structure is applied onto the window that protects the optics of an electronic device, such as a cellular phone or a tablet, such device, in the preferred embodiment, can function as a portable microscope. By altering parameters of the lens, such as the radius of curvature, it is possible to achieve a wide range of magnification.

Patent publication WO 2012/058641 A2 discloses a system and methods for enhancing the imaging of cameras included with wireless mobile devices, such as cellular phones or tablets. The system includes a releasable optical attachment for imaging skin surfaces and cavities of the body. The releasable optical attachment comprises elements for optical enhancement elements, such as magnifying lenses, illumination diverting elements, and filters. Images can be viewed and analyzed on the mobile device, or transmitted to another device or another location for analysis by a person or software. The results can be used to provide diagnosis, or for a variety of other applications, including image comparison over time and product recommendations.

Publication PLoSONE Vol. 6 issue 3 e17150 "Cell-Phone-Based Platform for Biomedical Device Development and Education Applications" (Zachary J. Smith, et al., March 2011) concerns the development of two adapters for a commercial cell phone, which transform the lens integrated into the phone and the image sensor into a microscope with 350× magnification and a visible-light spectrometer. The microscope can operate in polarized microscopy transmission mode and has shown to have a resolution of 1.5 microns and a usable visual field of approx. 150×150 microns without image processing, and approx. 350×350 microns with subsequent image processing.

SUMMARY OF THE INVENTION

It is one object of the present invention to provide an improved optical adapter which can overcome the drawbacks of the prior art.

More specifically, the object is to provide an optical adapter which has small dimensions and which can exploit the optics, the electronics and the software already present in the image acquisition device, while at the same time ensuring appropriate illumination of the object to be observed.

According to the present invention, this and other objects are achieved through an optical adapter.

It is to be understood that the appended claims are an integral part of the technical teachings provided in the following detailed description of the invention. In particular, some preferred embodiments of the present invention, which include some optional technical features, are defined herein.

Furthermore, in some exemplary embodiments of the present invention it is possible to provide an optical adapter which has a compact substrate structure, wherein a reflector is used in combination with a light guide system that brings the radiation generated by the LED light integrated into the device (thus constituting the illumination system thereof) in proximity to the object plane of a microobjective optically coupled to the objective lens of the camera built into the electronic device. Said microobjective has such a numerical aperture as to ensure a high resolution for microscopic images (in the order of a micron) and has such a radial physical dimension as to generate a distortion of the photographic field which is only limited to one sector thereof, thereby allowing wide-field determination of the area of the sample to be inspected in detail.

In some exemplary embodiments of the present invention, the substrate that includes the illuminator-microobjective assembly has a limited extension in the direction of the optical axis (e.g. shorter than 3 mm) and can be easily integrated into a protective cover of the device.

In some exemplary embodiments of the present invention, the substrate that includes the illuminator-microobjective assembly may possibly be made to translate on a support mounted on the device, e.g. a protective cover. This feature may allow for quick changes of the optical functionality of the electronic device, in order to switch from a "standard" camera application for macroscopic images to the application for microscopic observation, and vice versa.

In some exemplary embodiments of the present invention, the adapter can be easily integrated with optical fiber for image transfer (image fiber) and transformed into a portable endoscope or endomicroscope.

Further features and advantages of the present invention will become apparent from the following detailed description, which is supplied by way of non-limiting example with particular reference to the annexed drawings, which will be summarized below.

DETAILED DESCRIPTION OF THE INVENTION

Figure 1:
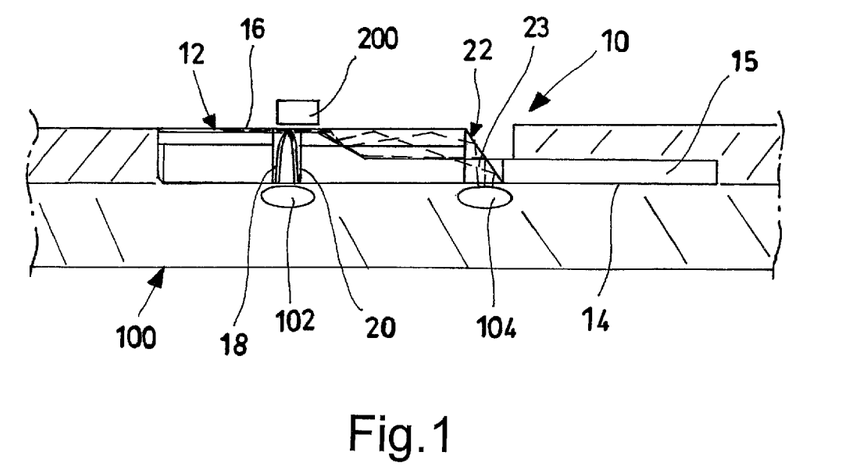
FIG. 1 is a longitudinal sectional view of an optical adapter made in accordance with an exemplary embodiment of the present invention.

With particular reference to FIG. 1, numeral 10 designates as a whole an optical adapter designed in accordance with an illustrative embodiment of the present invention.

The adapter 10 can be removably coupled to an image acquisition device, which is, by way of example, a smartphone 100. However, the image acquisition device must not necessarily be a cell phone or a smartphone, since it may be any device of any kind which can be used in an apparatus like a camera, a tablet, an augmented reality system (e.g. glasses equipped with such technology), or the like.

Particularly, but not necessarily, the adapter 10 is intended for use in microscopic observation. However, as will be apparent to a man skilled in the art in the light of the present description, optical adapters can be made in accordance with the present invention which provide a level of magnification that is not strictly of the microscopic type.

The adapter 10 comprises a support 12, which can be removably coupled to the image acquisition device, which in the illustrated embodiment is the smartphone 100. The support 12 comprises a substrate 15 made of substantially transparent material. Preferably, the substrate 15 is rigid and can be made as one piece or as a plurality of layers or parts joined together by means of, for example, an optically transparent adhesive.

Figure 2:
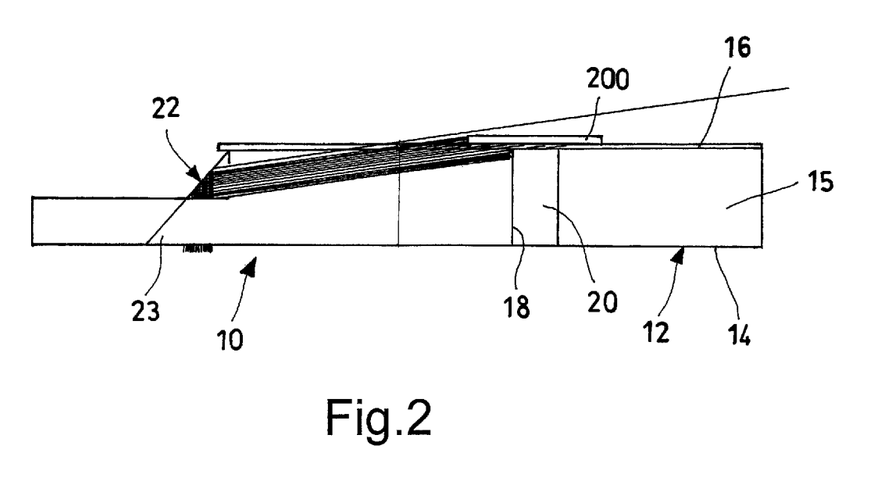
FIG. 2 is an elevation view of the optical adapter shown in FIG. 1.

The substrate 15 has a proximal surface 14 intended for facing towards the smartphone 100. In the illustrated embodiment, the proximal surface 14 is intended for being laid on the smartphone 100 (typically on the back face of the latter). In particular, the proximal surface 14 is so shaped as to match the surface of the smartphone 100 whereon said proximal surface 14 is to be laid. In the embodiment shown in FIGS. 1 and 2, the proximal surface 14 is substantially flat; however, as will be discussed hereafter, it may also be curved.

The substrate 15 also has a distal surface 16 located at a distance from the proximal surface 14. The distal surface 16 is intended for facing towards an object to be observed 200. Preferably, as will be described below, the distal surface 16 is also designed for resting on the object to be observed 200. In the embodiment shown in FIGS. 1 and 2, the distal surface 16 is substantially flat; however, as will be described hereafter, it may also be curved.

The support 12 further comprises an objective 20 located in a seat 18 obtained in the substrate 15. The objective 20 faces towards a photographic objective 102 of the image acquisition device, in particular of the smartphone 100. In the illustrated embodiment, the seat 18 passes through the substrate 15, crossing on one side the proximal surface 14 and on the other side the distal surface 16, thus creating a housing into which the objective 20 is inserted.

When in use, in particular, the objective 20 is in contact with or at a short distance from the glass that covers said photographic objective 102, with its optical axis parallel to the optical axis of the photographic objective 102, so as to realize an optical system capable of increasing the magnification normally obtainable by the smartphone 100. Therefore, the objective 20 is not necessarily coaxial with the optical axis of the photographic objective 102 integrated into the smartphone 100. However, it should be positioned within the field of view of the photographic objective 102 integrated with the electronic device.

Also, the objective 20 adapted to be inserted into the substrate 15 must not necessarily be made of the same material as the substrate 15.

The support 12 further comprises a reflector 22 located laterally relative to the objective 20. The reflector 22 is arranged for facing towards a light source, e.g. a LED light source 104, integrated into the smartphone 100. Also, the reflector 22 is configured for conveying the light emitted by the LED light source 104 in an oblique direction through the substrate 15, transversally towards the objective 20 and axially past the distal surface 16. In particular, the light emitted by the LED light source 104 is diverted by the reflector 22 in proximity to the focus of the objective 20, thus contributing to realizing an episcopic microscope with oblique illumination incident laterally relative to the objective 20.

Thanks to these technical features, the adapter 10 has small dimensions, can exploit the optics, the electronics and the software already present in the image acquisition device, and can also ensure appropriate illumination of the object to be observed 200.

The selection of the lens(es) making up the objective and the determination of the construction technique thereof are decisive factors to attain good optical performance. The autofocus capability of the photographic system of the image acquisition device, in this case the smartphone 100, allows for automatic calibration of the divergence of the collected light beam for optimized focusing. In particular, according to some exemplary embodiments of the present invention, the coupling between the objective 20 (which can thus realize a microobjective) and the photographic objective of the electronic device creates an optical system that is similar to the simplest version of a microscope with infinity-corrected optics.

With particular reference to FIGS. 3 to 8, the following will illustrate by way of example some typologies and variants of objectives 20 intended for use in combination with an optical adapter according to the present invention.

Preferably, the objective 20 may have a diameter of less than 2 mm and a focal length shorter than or equal to its diameter, thus allowing a maximum resolution of approx. 0.6 microns, at the wavelength of visible light. More generally, the use of an objective 20 with a short focal length (i.e. shorter than approx. 3-4 mm) provides an optical magnification that increases the software magnification due to the crop factor.

Preferably, in the objective 20 in use the numerical aperture NA may advantageously be in the range of approx. 0.2 to approx. 0.8, thus allowing a high (micrometric and sub-micrometric) resolution.

In the illustrated embodiment, the objective 20 may comprise a microlens or a plurality of microlenses. For example, the objective 20 comprises an array of microlenses (e.g. having lateral dimensions of less than approx. 2-3 mm) having a high numerical aperture NA (e.g. greater than approx. 0.2).

Figure 3:
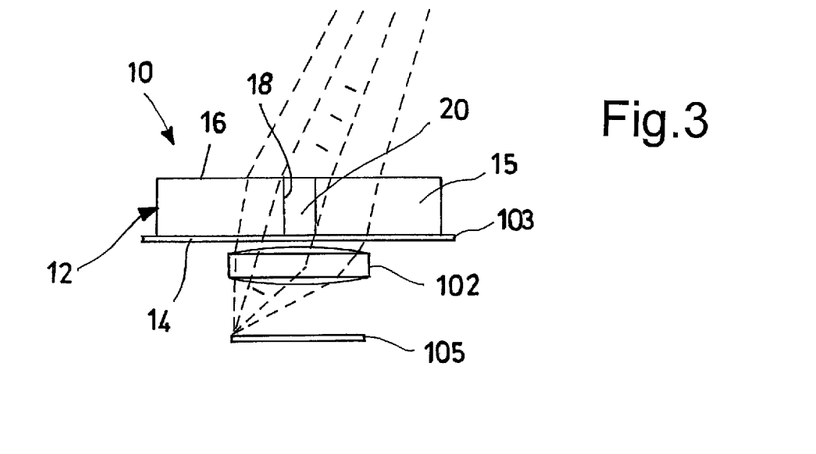
FIGS. 3 to 8 are schematic elevation views of different lens types intended for use in optical adapters made in accordance with various embodiments of the present invention.

According to the example shown in FIG. 3, when in use, the objective 20 is in contact with or at a short distance from the glass cover 103 of the photographic objective 102, with its optical axis parallel to the same optical axis of the photographic objective 102, thus realizing a system capable of increasing the magnification levels of the smartphone 100. Particularly, the objective 20 has a high numerical aperture and is characterized by a diameter smaller than the optical aperture of the objective 102, since it is inserted in the substrate 15 (the surfaces 14, 16 of which are preferably flat), and allows observation of the wide photographic field proper to the optical system integrated into the smartphone 100 also in the presence of said objective 20 positioned in front of the photographic objective 102. More in detail, according to FIG. 3, the light, the rays of which are represented as dashed lines, goes through the substrate 15, the glass 103 belonging to the photographic objective 102 of the image acquisition device (in this case, the smartphone 100), and the internal lens 104 of the photographic objective 102 of the device 100, and then reaches the image sensor 105. The light coming from the far field, intercepted by the region internal to the substrate 15 where the microscopy objective 20 is located, is not collected by the sensor 105 and is viewed as a dark area.

Figure 4:
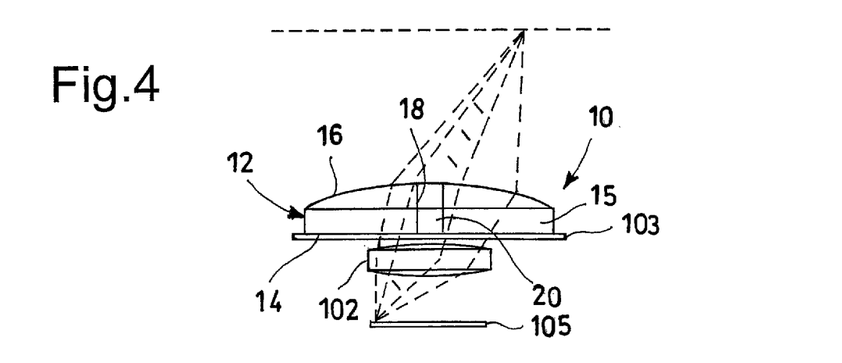
Figure 5:
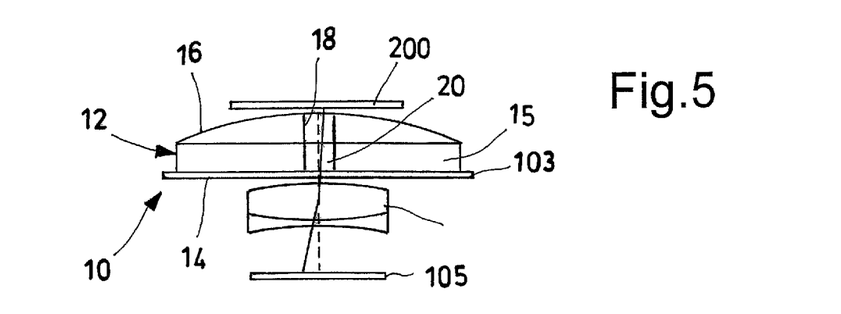

As shown by way of example in FIGS. 3, 4 and 5, the objective 20 realizes a microobjective with high numerical aperture NA that intersects only a part of the radiation incident from the wide field seen by the objective 102 integrated into the electronic device 100. For this reason, the wide field which is characteristic of the camera of the electronic device can be seen as a dark area corresponding to the solid angle occupied by the microobjective realized by the objective 20. In this manner, by moving the device closer to the sample to be observed it is possible to find the correct mutual positions of the sample and of the portable microscope, without one's attention being distracted from the screen. It should be noted that at least one of the surfaces 14, 16 of the substrate 12 into which the objective 20 is inserted may be curved (instead of planar as shown in the embodiment illustrated in FIGS. 1, 2 and 3). By way of example, the curvature of said surface faces outwards from the substrate 15. In FIGS. 4 and 5 only the distal surface 16 is curved. In other variants, however, the proximal surface 14 may have a similar curvature (on the side of the glass 103 of the device). The curvature of the surface of the support allows bringing the far field seen by the camera sensor outside the dark area generated by the objective 20, represented herein by the dashed line at the top. It is thus possible to obtain a magnification of the far field external to the one observed through the microobjective by a factor that is generally <30×, and to better determine the region containing the sample to be observed with a high resolution. This expedient shortens the focal length of the photographic optical system, thus further simplifying the positioning of the microscopic field without one's attention being distracted from the screen of the device.

In a preferred version, the objective 20 comprises a microlens of the gradient index (GRIN) rod type that ensures very good optical performance in terms of aberrations and planarity of the image field for the obtainable numerical aperture (NA), i.e. up to 0.5-0.6, with a limited diameter of the component. In the configuration that employs a GRIN lens as a terminal element of the microobjective, it is also possible to directly observe samples made of liquid or gel or immersed in a liquid, unlike those systems that use lenses with curved external surfaces designed for in-air operation, the function of which depends on the refraction index difference at the curved interface, thus not being able to operate in a liquid because the latter typically has a refraction index significantly different from 1. The system with the GRIN lens, on the contrary, can function also with the objective in contact with a liquid, since light deflection is gradual and is given by the variation of the refraction index within the medium. This allows the support, inclusive of the microobjective with the GRIN lens element, to be used also as a part of an immersion cover ensuring liquid tightness.

Of course, the magnification factor, and hence the width of the microscopic view field, can be varied by using GRIN rod lenses having different distributions of the refraction index along the radial direction of the rod.

Moreover, by appropriately selecting the distribution of the refraction index along the radial direction of the cylindrical body of the lens (which can be approximately described by the following mathematical function n(r)) and the length of said cylinder, it is possible to obtain desired values for the working distances of said microobjective. In order to use this optical system also for observing microscopy preparations on slides, i.e. with a transparent cover approximately 0.15 mm-0.25 mm thick, or elements immersed in liquids and/or three-dimensional bodies having a depth of a few tenths of a millimeter, it is therefore appropriate to employ n(r) and length parameters that provide a working distance of at least 0.25 mm in a material with a refraction index of approx. 1.45. One example of radial distribution that ensures this technical characteristic for a GRIN rod lens having a length of 2.15 mm (±0.1 mm) and a diameter of 1 mm is as follows:

$$n(r)=n_0+n_{r2}r^2+n_{r4}r^4,$$

where n0=1.629, nr2=−0.34, nr4=0.062.

Figure 6:
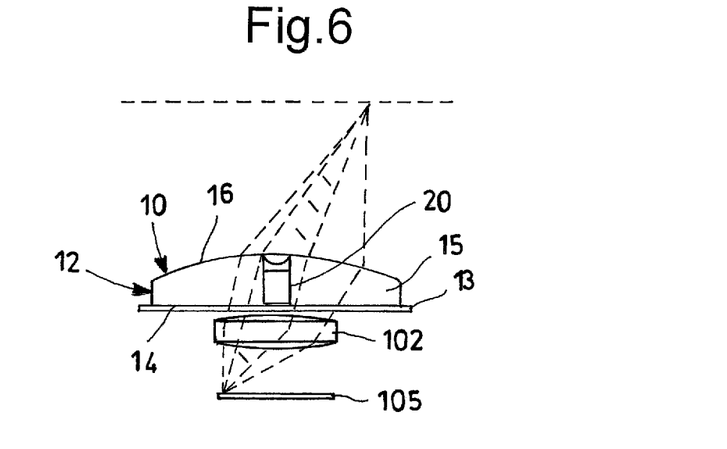

As shown by way of example in FIG. 6, the objective 20 may comprise a plurality of microlenses having a smaller diameter than that of the photographic objective 102 of the smartphone 100. The stacked microlenses may have planar or curved surfaces. In the variant illustrated in FIG. 6, the objective 20 may comprise a GRIN rod lens with the optional addition of a curved lens located at one end thereof.

Figure 7:
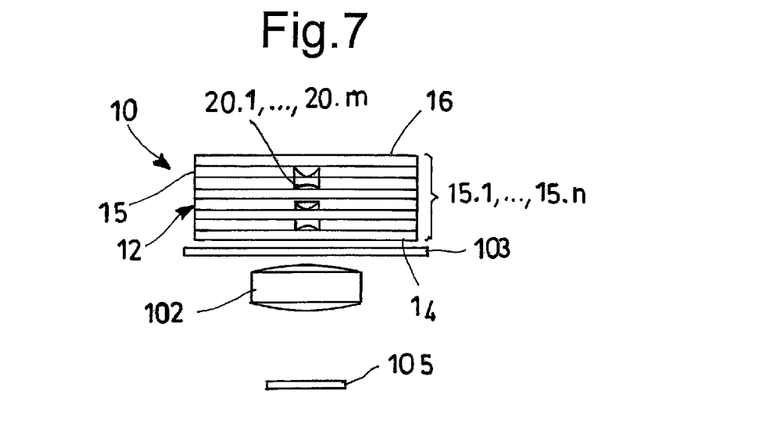

As shown by way of example in FIG. 7, the substrate 15 may consist of a plurality of thin layers 15.1, ..., 15.n having a controlled thickness, and the objective 20 may comprise, in turn, a plurality of microlenses 20.1, ..., 20.m, each one secured to a respective thin layer 15.1, ..., 15.n. The microlenses 20.1, ..., 20.m associated with the layers 15.1, ..., 15.n may be, for example, formed by moulding, glued to the layers 15.1, ..., 15.n, or obtained by deposition of transparent material. Furthermore, the thin layers 15.1, ..., 15.n may also have flat surfaces with no holes, adapted to operate as spacer foils having a refraction index other than 1, or may have flat surfaces with at least one seat for housing a respective microlens 20.1, ..., 20.m.

Figure 8:
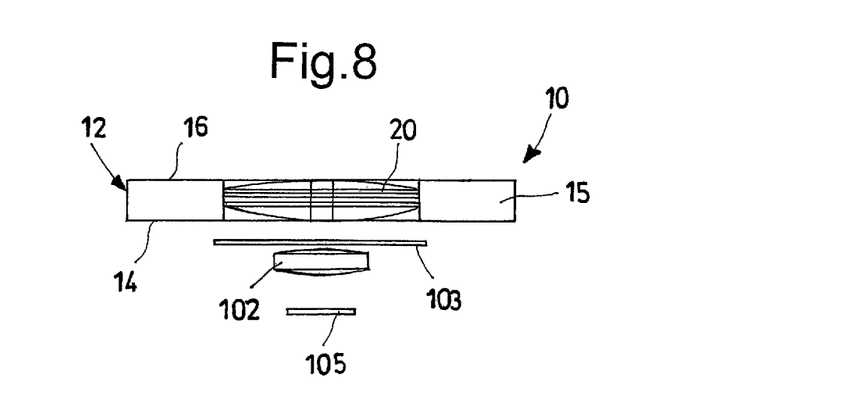

As shown by way of example in FIG. 8, the substrate 15 may also be structured in a more complex manner, comprising a plurality of sub-layers with elements having curved, planar or perforated surfaces (not numbered); in turn, these elements may be perforated or structured for housing the objective 20 (or microlenses 20.1, ..., 20.m) having a higher resolution, as previously described.

As a further optional measure concerning the objective 20, the image contrast can be increased by introducing an aperture diaphragm, possibly an adjustable one, for limiting the light incident on the photographic objective 102 from regions outside the high-magnification lens. In such a case, the seat 18 for the objective 20 may have opaque walls, so as to reduce the collection of light that might come from lateral directions, thus reducing the contrast of the microscopic image.

Optionally, the surfaces of the objective 20 may be coated with an antireflection coating, for increased contrast and improved signal-to-noise ratio.

As far as the reflector 22 is concerned, it preferably comprises a prism 23, e.g. having a triangular cross-section, which operates by total internal reflectance or which exploits a metallized surface or a surface made reflective by a high-reflectance coating. In the illustrated embodiment, the prism 23 has an oblique side for diverting the light coming from the LED light source 104. The oblique side is preferably oriented with an angle of approx. 45° relative to the distal surface 16.

Advantageously, the reflector 22 can be sized, particularly in terms of distances, curvature or inclination, according to the dimensional specifications of the electronic devices to which the optical adapter 10 is to be applied. Furthermore, by selecting an appropriate mutual distance between the reflector 22 and the object to be observed 200, the radiation will be mostly conveyed within the substrate 15 that carries the objective 20, which, since it consists of substantially transparent material, will thus become a unit having optomechanical functionalities.

Preferably, the support 12 is mounted on a bearing structure, e.g. a protective cover 24, configured for being removably fitted onto the smartphone 100. However, in further variant embodiments, as will be apparent to those skilled in the art, the bearing structure may have a shape and a function other than those of a protective cover.

In particular, the support 12 is movably mounted on the protective cover 24 between an operative condition, in which the objective 20 faces towards the photographic objective 102 and the reflector 22 faces towards the LED light source 104, and an inoperative condition, in which the objective 20 and the reflector 22 are away from the photographic objective 102 and from the LED light source 104. In the embodiment shown in FIGS. 11 and 12, the support 12 is translatable in a guided manner within a window 25 formed inside the protective cover 24.

Figure 11:
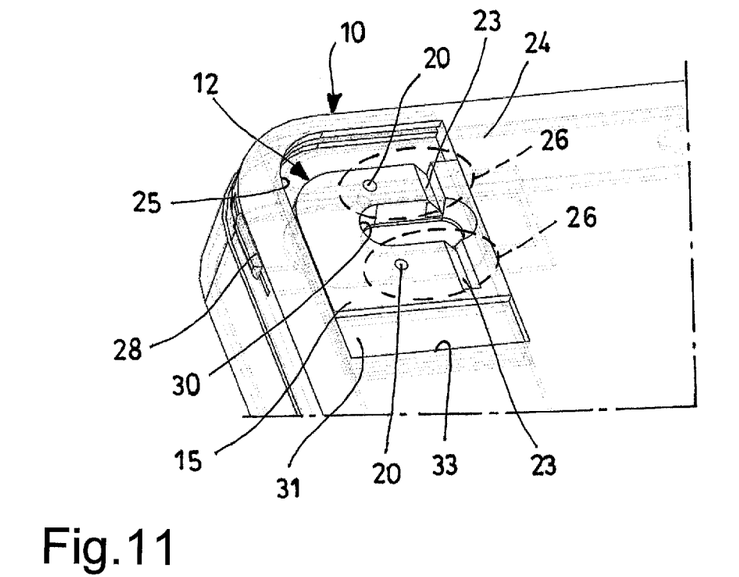
FIGS. 11 and 12 are, respectively, a perspective view and a plan view of an embodiment of a cell phone cover incorporating an optical adapter made in accordance with another embodiment of the present invention.
Figure 12:
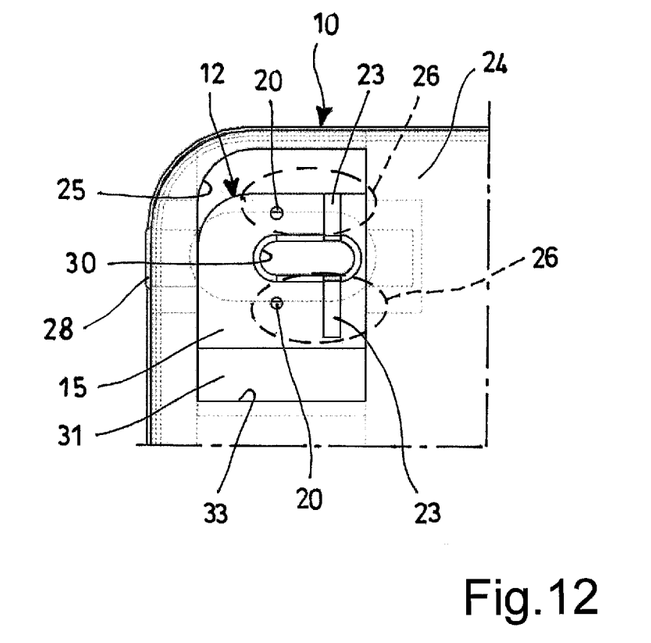

In the configuration illustrated in FIGS. 11 and 12, the support 12 including the substrate 15, the objective 20 and the reflector 22 can translate from the operative condition into the inoperative condition with a reduced travel, e.g. only a few millimeters. In this manner, the functionality of the smartphone 100 can be changed quickly and easily from macroscopic camera to high-resolution digital microscope.

In the embodiment illustrated in FIGS. 11 and 12, the support 12 comprises a plurality of optical assemblies 26, each one of said assemblies including a respective objective 20 and an associated reflector 22 having different optical properties. In particular, the support 12 is movable between a plurality of operative conditions, in each one of such operative conditions only one optical assembly 26 having its own objective 20 and its own reflector 22 aligned with the photographic objective 102 and with the LED light source 104, respectively. The possibility of translating the optical assemblies can thus be used to advantage to obtain an adapter 10 having functionalities that can be selected in a discrete manner, which includes a plurality of objectives 20, possibly with different characteristics and/or optical properties.

In the embodiment illustrated in FIGS. 11 and 12, the substrate 15 includes a grip element, e.g. a protrusion 28, which can be gripped by a user and moved between the different operative conditions. In particular, the protrusion 28 is formed as a slider. Preferably, said slider is located on one or two sides of the cover 24, extending past the smartphone 100, so that it can be easily operated even when the object to be observed 200 is close to the objective 20, without the latter having to be moved away from the device to clear the surface whereon the substrate 15 is located. In particular, the protrusion or slider 28 goes through the cover 24 and protrudes past the outer edges of the cover 24.

As an alternative to the above, the support 12 may be movable between the different operative conditions on the cover 24 by means of a motor, e.g. a linear electric motor.

In further embodiments, the support 12 may be mounted in a rotatable manner on the cover 24. According to one example (not shown), the substrate may be made as an element rotatable about a central axis, supported by the bearing structure. Around the central axis, the different optical assemblies, including the respective objective and reflector, are arranged in a sunburst pattern, and can in turn be rotated into the position facing towards the photographic objective and the light source of the image acquisition device. In this configuration, it is appropriate that the central axis is offset and away from the optical aperture of the image acquisition device.

Preferably, also when the adapter 10 is operative in the "microscope" operative mode, the wide-field vision characteristics proper to the photographic mode can for the most part be preserved. The sample that needs to be observed with high magnification levels can thus be easily and accurately found, and videos can be made which show the switching from a macroscopic scale to the microscopic one, so that the device will not be very invasive.

In the embodiment illustrated in FIGS. 11 and 12, the support 12 has two optical assemblies 26, each one of such assemblies including a respective objective 20 and an associated reflector 23 and having different optical properties. Between such optical assemblies 26, an aperture is formed on the substrate 15, through which the photographic objective 102 and the LED light source 104 face outwards through the substrate 15 when the support 12 is in the inoperative condition.

Preferably, there may be some guiding elements, e.g. laminar protrusions 31 projecting from the substrate 15 and appropriately sized. The guiding elements, i.e. the laminar protrusions 31 can be inserted into matching slots 33 formed inside the cover 24. In particular, said slots 33 may be formed through the inner edge of the window 25 when the support 12 is in one of the operative conditions.

Figure 13:
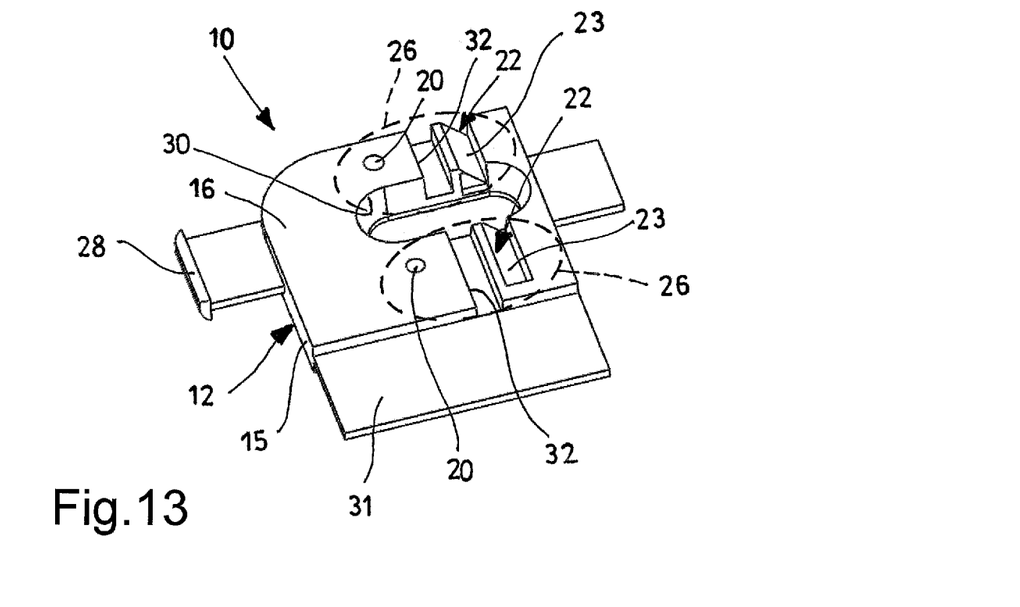
FIGS. 13 and 14 are partial perspective views of two further embodiments of an adapter made in accordance with the present invention.

Preferably, the substrate 15 has a housing 32 along the optical path of the illumination light directed from the reflector 22 towards the object plane of the objective 20. Into the housing 32 additional optical elements can be inserted, which are configured for filtering or diffusing the illumination light directed from the reflector 22 towards the object plane of the objective 20. In particular, said housing 32 has a seat that intersects the optical path of illumination. In the embodiment shown in FIGS. 13 and 14, which employs two optical assemblies (not numbered), wherein each optical assembly includes a respective objective 20 and an associated reflector 22, the substrate 15 also has a pair of housings 32.

Figure 14:
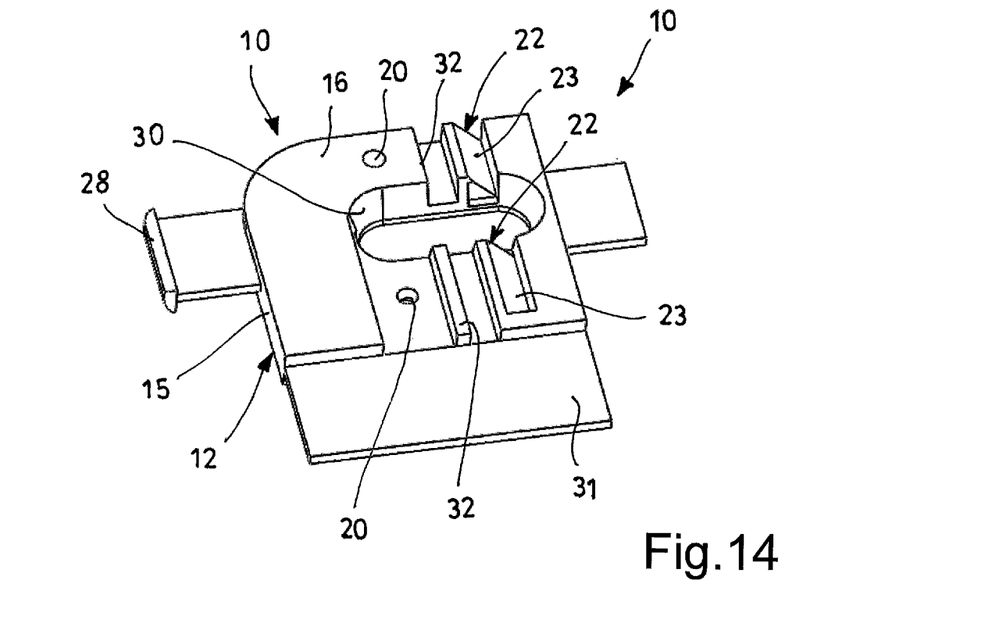

In the embodiment illustrated in FIG. 14, the substrate 15 has a thickness (i.e. the distance between the surfaces 14, 16) at one of the optical assemblies 26, associated with one of the objectives 20, which is different from the thickness of the other one of the optical assemblies 26, associated with the other one of the objectives 20. This expedient can facilitate the determination of the correct focal plane for each objective 20 of the optical assemblies 26, and can be particularly useful when objectives 20 having different working distances are located on the same substrate 15, so that the support plane can be the same and the object to be observed 200 can be focused easily in both cases. For example, this expedient may turn out to be useful in a configuration wherein on the same substrate there are a first objective having a magnification factor of 120× (with a short working distance) and a second objective having a magnification factor of 30× (with a longer working distance).

In further variant embodiments (not shown), a plurality of objectives 20 having a high numerical aperture can be positioned simultaneously in parallel in front of the photographic objective 102, for cooperating simultaneously with one same reflector 22; in this manner, one can obtain multiple microscopic fields of view with different magnification levels.

Figure 9:
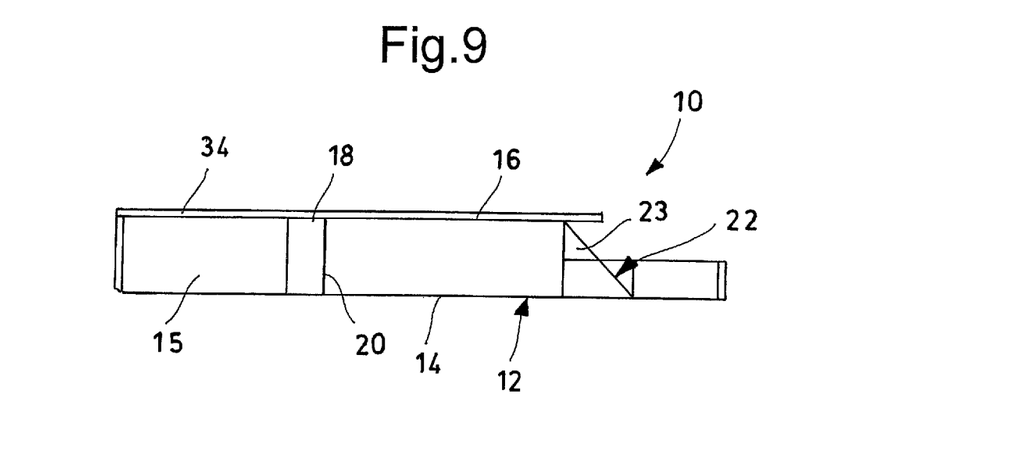
FIGS. 9 and 10 are elevation views of two further embodiments of an optical adapter made in accordance with the present invention.
Figure 10:
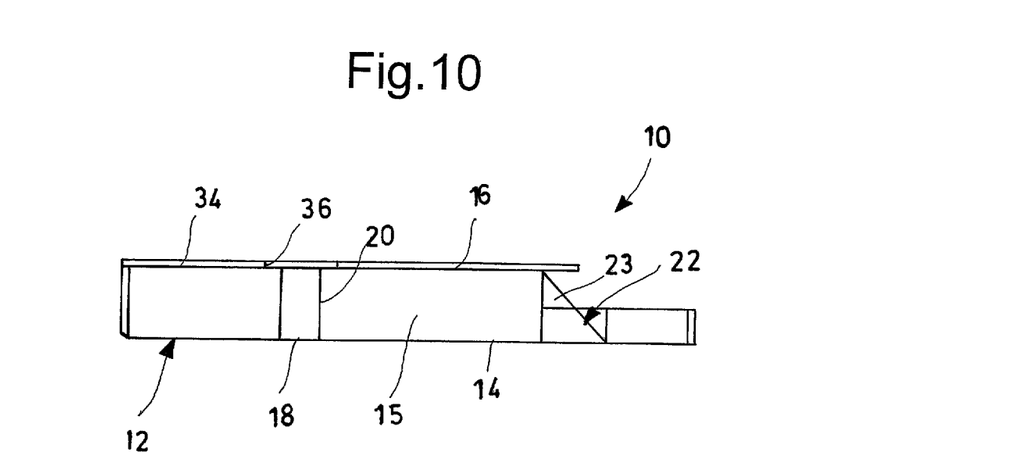

In the embodiment illustrated in FIGS. 9 and 10, the distal surface 16 can be coated with a thin transparent layer or film 34, possibly a removable one, functioning as a protector and a spacer to allow observing the sample in contact with said spacer, thus facilitating the use of the instrument. As previously discussed, the adapter 10—the dimensions of which are very small, with working distances of less than 1 mm for the objective (20)—makes it possible to lay the surface of the object to be observed 200 on the coating layer 34 (which may be removable, to allow observation through slides having a thickness comparable to that of the coating layer 34). For example, the coating layer 34 has a thickness in the range of 0.05 mm to 0.5 mm and can be positioned on the photographic objective 102 to allow observation of the surface of bodies placed in contact with or in proximity to it.

The coating layer 34 may be a self-adhesive transparent film (e.g. of the type commonly used for protecting the displays of electronic devices), which either coats the surface of the objective 20 or has a hole 36 matching the surface of the objective 20, in which case it will only function as a spacer. This coating layer 34 can be easily removed when samples in the form of standard microscopy preparations have to be observed, covered by an object covering slide, whether in transmission or reflection mode. With such a configuration, the sample to be analyzed will be in contact with or in close proximity to the device, with no mechanical spacers significantly protruding (thickness comparable to the body of the electronic device) from the body of the image acquisition device.

Figure 15:
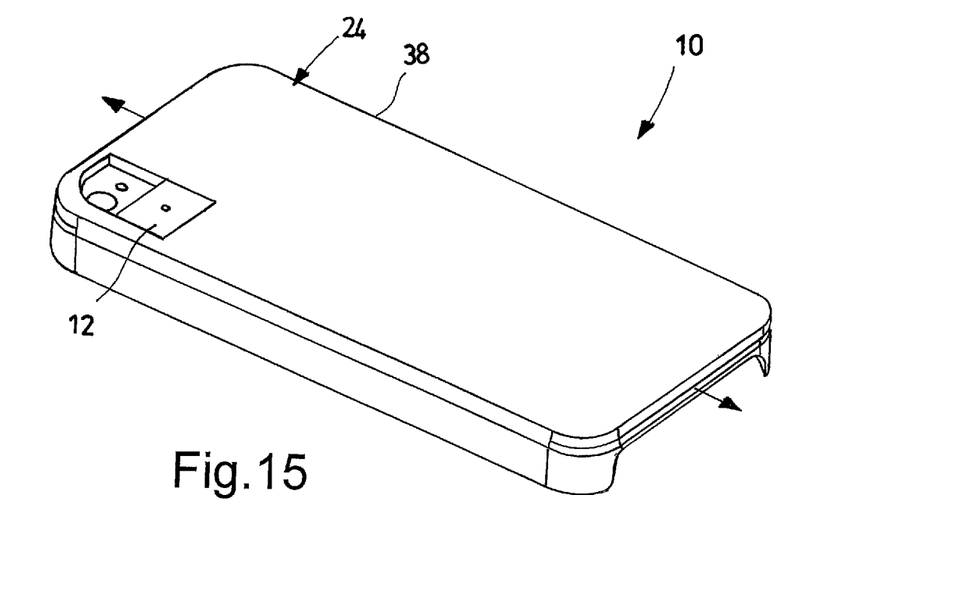
FIGS. 15 and 16 are perspective views of two different cell phone covers incorporating embodiments of an optical adapter made in accordance with the present invention.

According to the embodiment illustrated in FIG. 15, the support 12 is integral with a back wall 38 of the cover 24, which is slidable relative to the rest of the latter. Optionally, the back wall 38 is longer in the direction of translation and can be locked in positions providing the desired optical alignment of the objective 20 with respect to the photographic objective 102 of the smartphone 100.

Figure 16:
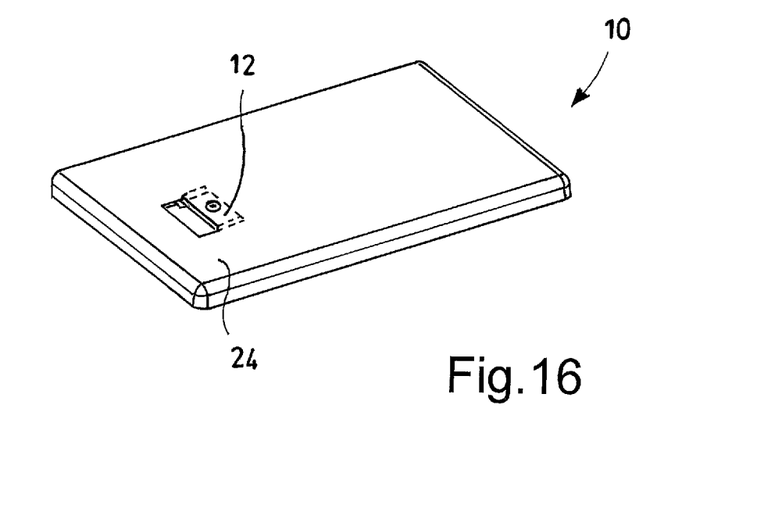

According to the embodiment illustrated in FIG. 16, the support 12 is hinged to the cover 24, so that it can be switched between the operative condition (in which the objective 20 and the reflector 22 are superimposed on the photographic objective 102 and on the LED light source 104) and the inoperative condition (in which the substrate 12 is turned outwards from the cover 24, thereby moving the objective 20 and the reflector 22 away from the photographic objective 102 and from the LED light source 104).

According to a further embodiment (not shown), the adapter may comprise an endoscope, i.e. a microobjective and a light guide, e.g. a beam of optical fibers. The light guide is optically coupled to the microobjective on one side and to the objective 20 on the other side, so as to be able to transfer the image collected by the microobjective onto the object plane of the objective 20 through the beam of optical fibers.

Preferably, the microobjective of the microendoscope comprises a GRIN element, e.g. a GRIN rod. In particular, said GRIN rod may have a length equal to approximately ½ pitch or multiples thereof, or other types of microscopic optical systems. In such a configuration, the system as a whole becomes a flexible portable endoscope that can be integrated with an image acquisition device such as a smartphone or a tablet.

The use of a beam of optical fibers and a GRIN rod lens will allow the creation of endoscopes having a diameter smaller than one millimeter, while maintaining a high optical resolution.

In such configurations for endoscopy or microendoscopy, the LED light source associated with the device (e.g. a smartphone) can transfer the light in proximity to the terminal end of a further light guide, different from the one used for image transportation. Said further light guide may be an optical fiber rigidly connected to the beam of fibers that transports the image reflected by the sample towards the camera sensor.

The overall optical performance of the microscopic, endoscopic or microendoscopic systems can be improved by introducing aspherical corrective lenses for correcting the aberrations of the microobjectives (GRIN rod lenses). These lenses can be manufactured, for example, by using microprocessing techniques such as two-photon photolithography or material ablation by laser pulses, followed by chemical etching to ensure high dimensional accuracy.

Of course, without prejudice to the principle of the invention, the forms of embodiment and the implementation details may be extensively varied from those described and illustrated herein by way of non-limiting example, without however departing from the scope of the invention.

The invention claimed is:

1. An optical adapter which can be coupled to an image acquisition device for microscopic observation; said adapter comprising:
   a support made of substantially transparent material, which can be removably coupled to said device; said support having a proximal surface facing towards said device and a distal surface located at a distance from said proximal surface and facing towards an object to be observed; said support having:
   a substantially optically transparent substrate,
   an objective located in a seat in said substrate and facing towards an objective of said device, and
   a reflector located laterally relative to said objective of said substrate and arranged to face towards a light source integrated into said device and conveying light emitted by said light source in an oblique direction, transversally towards said objective of said substrate and axially past said distal surface;
   wherein said substrate has at least one curved surface adapted for shortening the focal distance of the photographic field collected by said objective of said device, outside a solid angle of radiation intersected by said objective of said substrate;
   wherein said objective of said substrate comprises at least one microlens and
   wherein said microlens is a gradient index rod lens (GRIN).

2. The optical adapter according to claim 1, wherein said substrate is made as one piece.

3. The optical adapter according to claim 1, wherein said substrate comprises a plurality of layers joined together.

4. The optical adapter according to claim 1, wherein said reflector comprises a prism, which has an oblique side for deflecting said light.

5. The optical adapter according to claim 1, wherein the substrate has at least one housing located in the optical path of the illuminating light directed by the reflector towards the object plane of the objective of said substrate; into said at least one housing at least one additional optical element can be inserted, which is configured for filtering or diffusing said light.

6. An optical adapter couplable to an image acquisition device for microscopic observation; said adapter comprising:
   a support made of substantially transparent material, which can be removably coupled to said device; said support having a proximal surface facing towards said device and a distal surface located at a distance from said proximal surface and facing towards an object to be observed; said support having:
   a substantially optically transparent substrate;
   an objective located in a seat of said substrate and facing towards an objective of said device,
   a reflector located laterally relative to said objective of said substrate and arranged to face towards a light source integrated into said device and conveying light emitted by said light source in an oblique direction, transversally towards said objective of said substrate and axially past said distal surface; and
   a bearing structure removably mounted on said device; said support being movably mounted on said bearing structure between an operative condition, in which said objective of said substrate is arranged for facing towards the objective of said device and the reflector is arranged to face towards the light source, and an inoperative condition, in which the objective of said substrate and the reflector are arranged to move away from the objective of said device and from the light source;
   wherein said substrate has at least one curved surface adapted for shortening the focal distance of the photographic field collected by said objective of said device, outside a solid angle of radiation intersected by said objective of said substrate.

7. The optical adapter according to claim 6, wherein the substrate comprises at least one pair of optical assemblies, each one of said optical assemblies including a respective objective of said substrate and an associated reflector having different optical properties; the support is movable between a plurality of operative conditions, in each one of said operative conditions only one optical assembly having an own objective of said substrate and an own reflector arranged for being aligned with the objective of said device and with the LED light source, respectively.

8. The optical adapter according to claim 7, wherein an aperture is formed between said optical assemblies on the substrate, through which the objective of said device and the LED light source will face outwards through the substrate when the support is moved into the inoperative condition.

9. An optical adapter couplable to an image acquisition device for microscopic observation; said adapter comprising:
   a support made of substantially transparent material, which can be removably coupled to said device; said support having a proximal surface facing towards said device and a distal surface located at a distance from said proximal surface and facing towards an object to be observed; said support having:
   a substantially optically transparent substrate;
   an objective located in a seat in said substrate and facing towards an objective of said device; and
   a reflector located laterally relative to said objective of said substrate and arranged to face towards a light source integrated into said device and conveying light emitted by said light source in an oblique direction, transversally towards said objective of said substrate and axially past said distal surface;
   wherein said substrate has at least one curved surface adapted for shortening the focal distance of the photographic field collected by said objective of said device, outside a solid angle of radiation intersected by said objective of said substrate;
   wherein the distal surface is coated with a removable transparent coating layer having a protection function.

10. An optical adapter couplable to an image acquisition device for microscopic observation; said adapter comprising:
- a support made of substantially transparent material, which can be removably coupled to said device; said support having a proximal surface facing towards said device and a distal surface located at a distance from said proximal surface and facing towards an object to be observed; said support having:
  - a substantially optically transparent substrate;
  - an objective located in a seat in said substrate and facing towards an objective of said device; and
  - a reflector located laterally relative to said objective of said substrate and arranged to face towards a light source integrated into said device and conveying light emitted by said light source in an oblique direction, transversally towards said objective of said substrate and axially past said distal surface;
  - a microobjective and a light guide optically coupled to said microobjective on one side and to the objective of said substrate on the other side, to transfer the image collected by the microobjective onto the object plane of the objective of said substrate through said light guide;
- wherein said substrate has at least one curved surface adapted for shortening the focal distance of the photographic field collected by said objective of said device, outside a solid angle of radiation intersected by said objective of said substrate.

11. The optical adapter according to claim 10, further comprising a further light guide optically coupled to the reflector on one side and capable, on the other side, to transfer the illuminating light coming from said reflector, directing the illuminating light towards the object plane of said microobjective.

* * * * *